(12) United States Patent
Shen et al.

(10) Patent No.: US 8,615,286 B2
(45) Date of Patent: Dec. 24, 2013

(54) IN VIVO SENSOR FOR DETECTING BONE SURFACE

(75) Inventors: Feimo Shen, Milpitas, CA (US); Youngbae Park, Fremont, CA (US)

(73) Assignee: Curexo Technology Corporation, Fremont, CA (US)

( * ) Notice: Subject to any disclaimer, the term of this patent is extended or adjusted under 35 U.S.C. 154(b) by 0 days.

(21) Appl. No.: 12/836,280

(22) Filed: Jul. 14, 2010

(65) Prior Publication Data
US 2011/0112397 A1     May 12, 2011

Related U.S. Application Data

(60) Provisional application No. 61/270,932, filed on Jul. 15, 2009.

(51) Int. Cl.
*A61B 5/055*     (2006.01)

(52) U.S. Cl.
USPC .................................................. 600/424

(58) Field of Classification Search
USPC ............................................ 600/424; 606/131
See application file for complete search history.

(56) References Cited

U.S. PATENT DOCUMENTS

| | | | |
|---|---|---|---|
| 6,033,415 A | 3/2000 | Mittelstadt et al. | |
| 6,526,642 B2 * | 3/2003 | Sausner | 29/407.05 |
| 2007/0106306 A1 * | 5/2007 | Bodduluri et al. | 606/133 |

* cited by examiner

*Primary Examiner* — Michael Rozanski
(74) *Attorney, Agent, or Firm* — Pandiscio & Pandiscio

(57) ABSTRACT

A device and a method are described for finding the location of a bone surface in patients or living animals by using a thin probe equipped with bone contacting detection functionality for a minimally invasive procedure.

4 Claims, 7 Drawing Sheets

IN VIVO SENSOR FOR DETECTING BONE SURFACE

REFERENCE TO PENDING PRIOR PATENT APPLICATION

This patent application claims benefit of prior U.S. Provisional Patent Application Ser. No. 61/270,932, filed Jul. 15, 2009 by Feimo Shen et al. for IN VIVO SENSOR FOR DETECTING BONE SURFACE, which patent application is hereby incorporated herein by reference.

FIELD OF THE INVENTION

The present invention relates to surgical methods and apparatus in general, and more particularly to a novel method and apparatus for facilitating surgical bone interventions by providing accurate bone location with minimal invasiveness to the patient.

BACKGROUND OF THE INVENTION

When performing surgical bone interventions such as implanting a prosthesis into a bone, milling to resurface a bone, cutting the bone or drilling of the bone, an accurate recognition of the spatial position of the operative bone is necessary for proper surgery. In traditional surgery, the surgeon recognizes bone position by visual inspection based on his knowledge and experience.

Recently, computer-aided orthopedic surgery and related instruments have been introduced. Using such a system, the planning and execution of the surgery can be aided, especially with the recognition of and tracking of the spatial position of the bone.

For the recognition of the spatial location of the interested bone, several methods have been devised and used. U.S. Pat. No. 6,033,415 describes a method used to recognize or register the location of the bone by digitizing the surface of the bone, i.e., by contacting a probe against the bony surface at a plurality of locations. Once the surface of the bone has been digitized, the acquired data points can be compared against a pre-acquired model of the bone so as to identify the position of the bone in space. With the method of U.S. Pat. No. 6,033,415, the probe can digitize an exposed bony surface, or it can digitize the bony surface by puncturing the skin and contacting the bone. In practice, puncturing of the skin is desirable in some cases so as to reduce the size of the incision made in the patient; but also, it can be challenging to accurately digitize the bony surface through puncturing of the skin and tissue because the "view" is very limited and the tactile feedback is often compromised by the skin, muscle and periosteum. And, also, it has been found that the diameter of the skin puncture is very critical to the amount of pain presented to the patient and the subsequent recovery of the patient after the surgery.

By providing a new method to detect the contact of a thin probe to the bony surface, the digitization of the bone can be done with a minimum amount of invasiveness and it can yield significant patient benefit in the form of accurate and safe surgical results and a fast recovery.

PRIOR ART

1. Manual Palpating with Metal Probe (U.S. Pat. No. 6,033,415)

During a robotic arthroplasty surgery, the bone of operation needs to be registered with the robot cutter coordinate system. One method of registration is first obtaining the surface features of the bone and then performing a search for a 3D spatial transformation in order to identify the current position of the bone in the robot cutter coordinate system. In the current ROBODOC setup (Curexo Technology Corporation, Sacramento, Calif.), the digitizer uses a thick (4.97 mm diameter) steel probe with a pointed tip. In order to reach the bone surface during surgery, a relatively large area of the bone needs to be exposed. Furthermore, stabbing wounds have to be introduced to reveal the bone surface at certain distal places. The surgeon uses the steel probe to palpate for the surface of the bone. Therefore, the accuracy and precision of this method largely depends on the experience of the surgeon and his or her consistency.

2. Laser Scanning with Laser Range Finder

Contactless methods, such as rangefinding with laser scanners, are a great way of sterile distance detection that do not cause mechanical perturbations. However, during certain surgeries with particle accumulation on the bone surface (e.g., due to nearby bone drilling and milling) unwanted irregularities can accumulate on top of the surface of interest, rendering the laser rangefinding inaccurate. Furthermore, laser scanners typically cannot detect true cortical bone because it is often covered by a periosteum layer or cartilage. Therefore, the surfaces found by laser scanners are the ones of the outermost layers of the bone, rather than the actual cortical bone surfaces. However, since the surface models generated from scans are usually based on detecting cortical bone, it is crucial that the detection method accurately identify cortical bone surfaces in order for correct registration to be achieved. Hence, laser scanners do not permit perfect registration to be achieved, since they typically cannot accurately identify cortical bone surfaces.

BRIEF DESCRIPTION OF THE FIGURES AND TABLE

Figure 3:
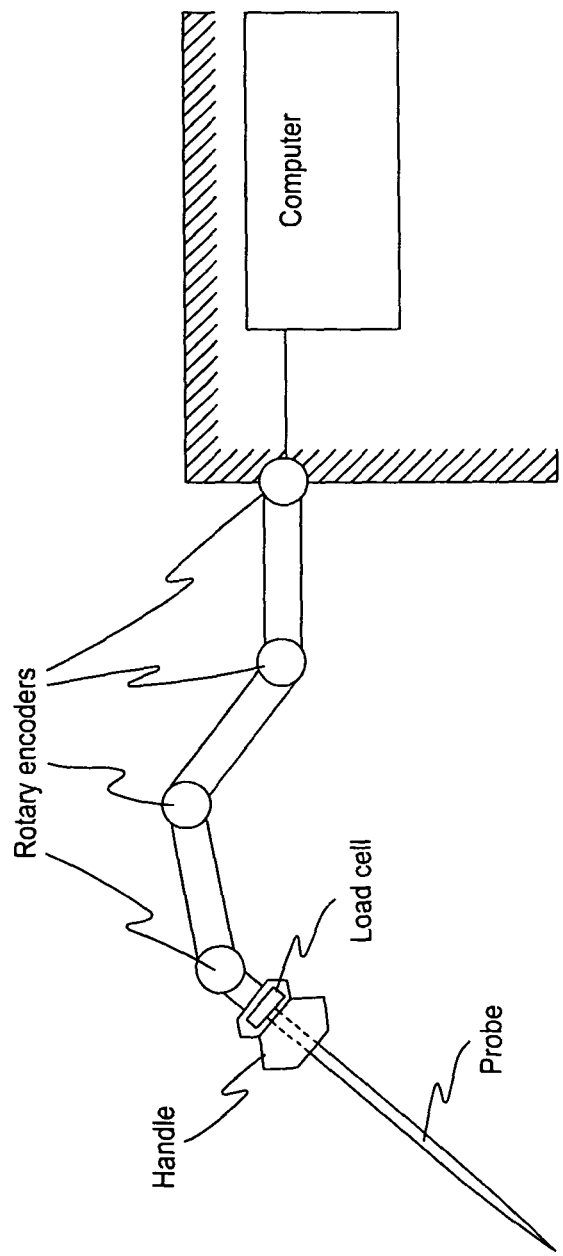
Figure 4:
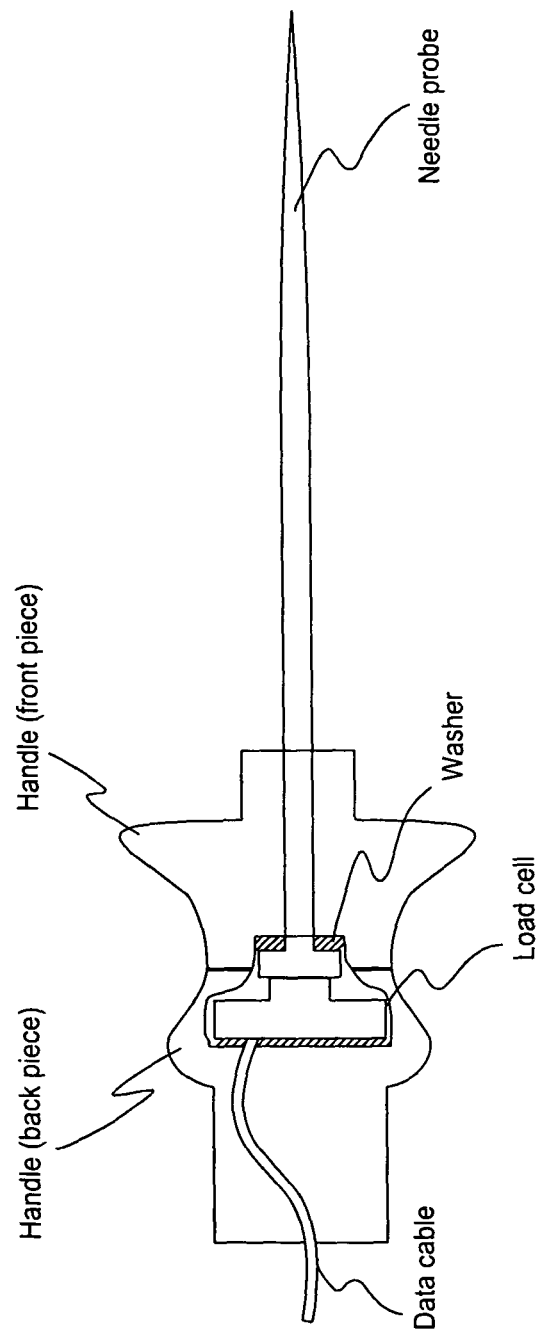
Figure 5:
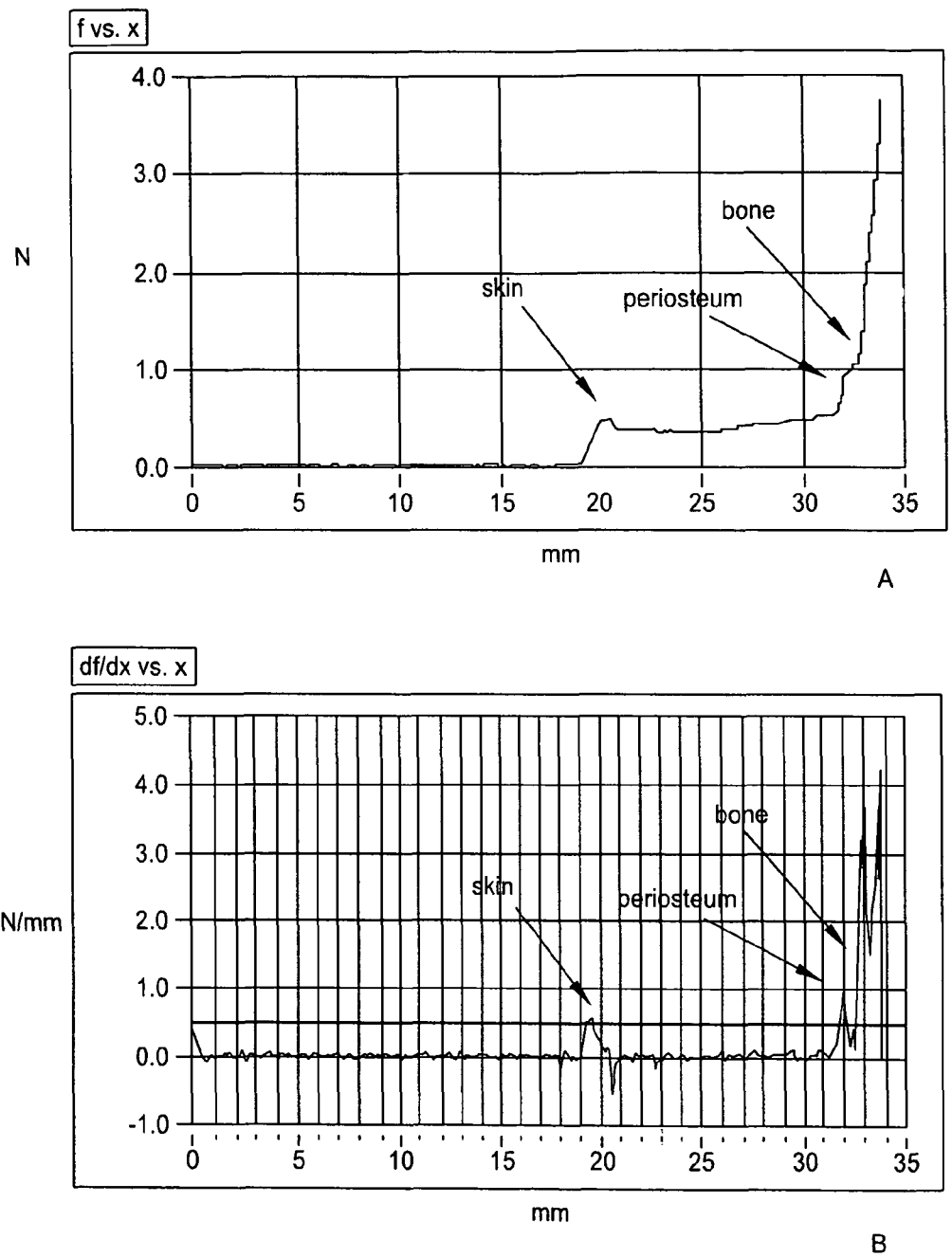
Figure 6:
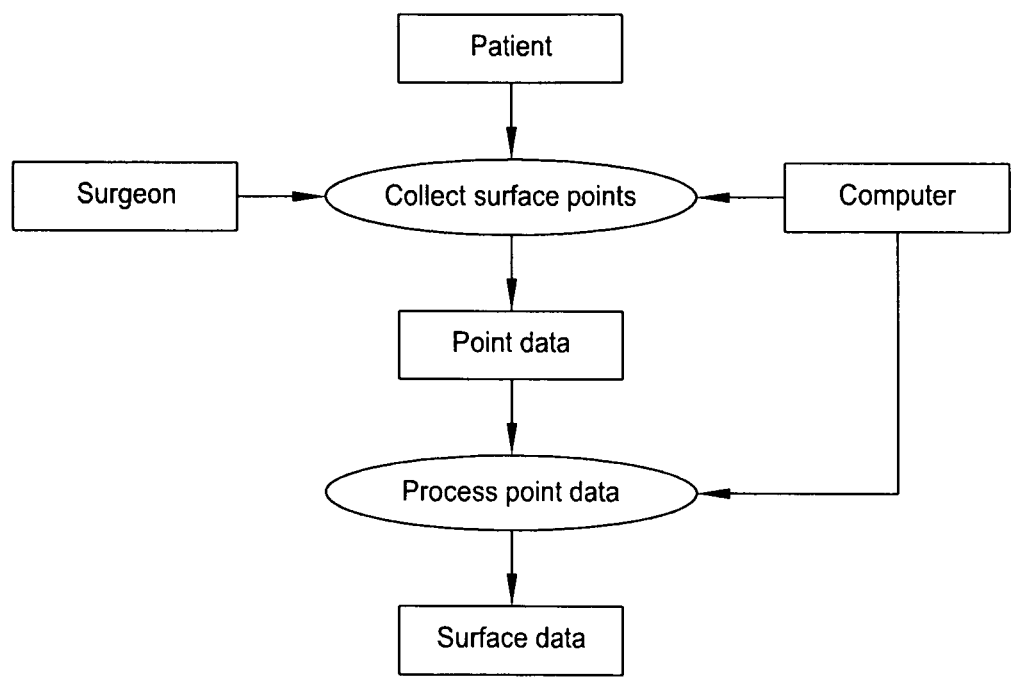
Figure 7:
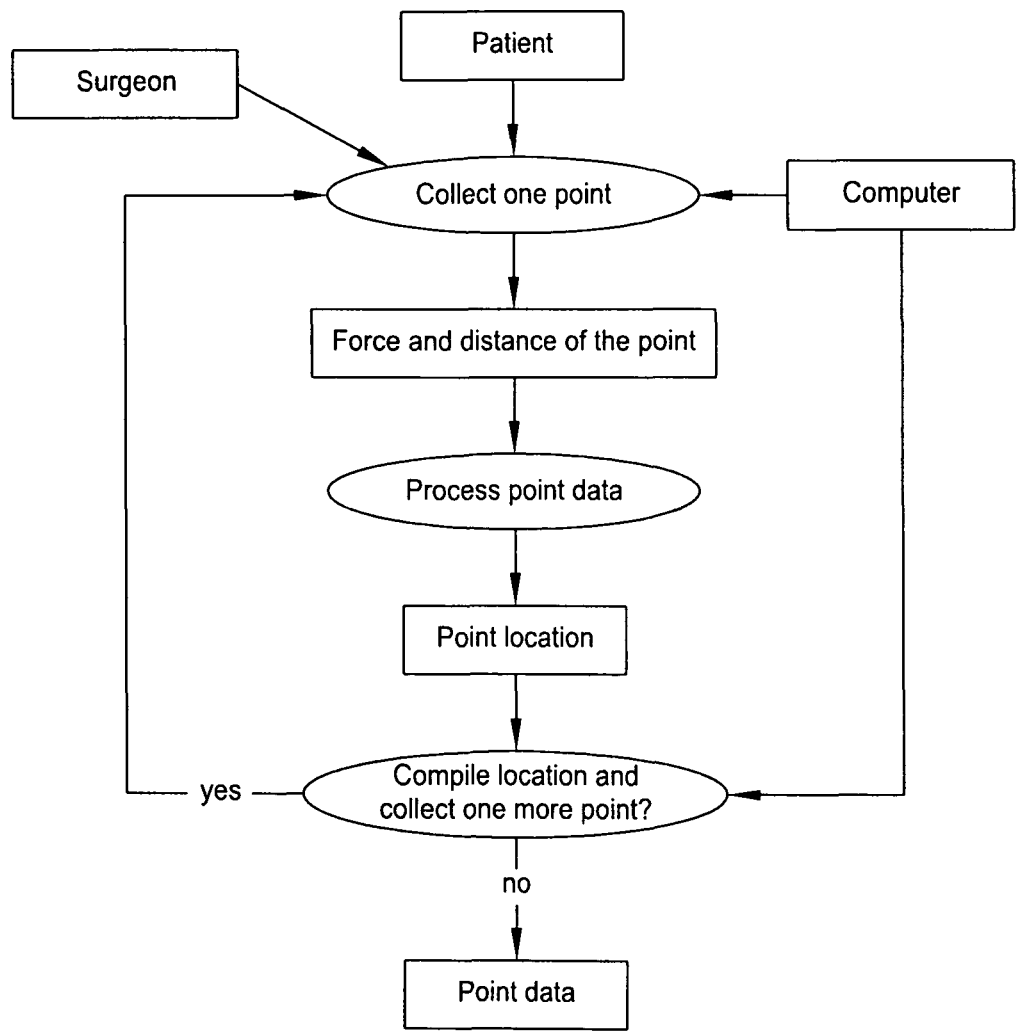

FIG. 3 shows an example of the probe tracking system. The probe is installed on a robot arm with revolute joints. The base of the robot arm is attached on a fixture. A load cell that resides in a handle is attached to the needle probe. A computer receives the rotary encoder signals to compute the probe tip position;

FIG. 4 shows a detailed schematic diagram of the needle probe-force sensor assembly. The data cable provides the force the load cell senses from the needle probe;

FIG. 5 shows a software plot of the force profile (Panel A) and the derivative of the force (Panel B) from a typical experiment;

FIG. 6 shows an object process diagram of the overall processes involved in the invention;

FIG. 7 shows the detailed processes inside the action block entitled "Collect surface points" in FIG. 6; and TABLE 1 shows the results from experiments with animal samples.

SUMMARY OF THE INVENTION

In this invention, there is disclosed a probe which has means to record its spatial location and also means to detect contact of the probe with the bony surface.

For the probe itself, it is a probe which is intended to have mechanical contact with the bony surface and is thin and long so that it can be introduced through the soft tissue until it contacts the bony surface.

The means to record the spatial location of the probe recognizes the location of the probe tip so that when the probe is in contact with the bone, that location will be digitized and processed by the computer-aided surgery system. For the recognition of the probe location, a mechanical arm type digitizer, an infra-red (IR) marker tracking camera, a magnetic tracker or any other appropriate method and/or apparatus can be used.

The means to detect contact of the probe with the bony surface uses a force sensor to detect the resistance of the material encountered by the probe, a piezoelectric sensor to measure the natural frequency of the probe, an ultrasound sensor to measure the material property at the tip of the probe or any other appropriate method and/or apparatus can be used.

In one form of the present invention, there is provided apparatus for determining the position, in three dimensional space, of a bone covered by soft tissue, said apparatus comprising:

a needle having a tip for penetrating soft tissue;

position-determining means for determining the position of said tip of said needle in three-dimensional space;

force-sensing means for sensing the force encountered by said tip of said needle;

discriminating means for discriminating between (i) the force encountered by said tip of said needle when said tip of said needle is engaging soft tissue, and (ii) the force encountered by said tip of said needle when said tip of said needle is engaging bone; and recording means for recording the position of said tip of said needle in three dimensional space when said discriminating means indicate that said tip of said needle is engaging bone.

In another form of the present invention, there is provided a method for determining the position, in three dimensional space, of a bone covered by soft tissue, said method comprising:

directing the tip of a needle through the soft tissue and toward the bone while sensing the level of force encountered by said tip of said needle;

identifying a spike in the level of force encountered by said tip of said needle, wherein the spike is reflective of said tip of said needle encountering bone; and recording the position of said tip of said needle in three-dimensional space when said spike is identified.

In another form of the present invention, there is provided apparatus for determining the position, in three dimensional space, of a first type of tissue which is covered by a second type of tissue, wherein said first type of tissue has a greater resistance to penetration than said second type of tissue, said apparatus comprising:

a needle having a tip for penetrating tissue;

position-determining means for determining the position of said tip of said needle in three-dimensional space;

force-sensing means for sensing the force encountered by said tip of said needle when engaging tissue;

discriminating means for discriminating between (i) the force encountered by said tip of said needle when said tip of said needle is engaging said first type of tissue, and (ii) the force encountered by said tip of said needle when said tip of said needle is engaging said second type of tissue; and recording means for recording the position of said tip of said needle in three dimensional space when said discriminating means indicate that said tip of said needle is engaging said first type of tissue.

In another form of the present invention, there is provided a method for determining the position, in three dimensional space, of a first type of tissue which is covered by a second type of tissue, wherein said first type of tissue has a greater resistance to penetration than said second type of tissue, said method comprising:

directing the tip of a needle through the second type of tissue and toward the first type of tissue while sensing the level of force encountered by said tip of said needle;

identifying a change in the level of force encountered by said tip of said needle, wherein said change is reflective of said tip of said needle encountering said first type of tissue; and recording the position of said tip of said needle in three-dimensional space when said change is identified.

In the following sections, a detailed description of the invention will be provided by exemplary embodiments.

DETAILED DESCRIPTION OF THE PREFERRED EMBODIMENTS OF THE INVENTION

An exemplary embodiment of the invention will now be described that serves to provide significant clinical improvements for joint replacement surgery, particularly to achieve minimally invasiveness.

A resistant force-based approach can be used to detect the interface between two layers of tissue with dissimilar hardness, using computer software that calculates the rate of change of force with respect to distance. During surgery, in order to determine the location of the bone surface without exposing the bone, the doctor uses the setup shown in FIGS. 1 and 3. The doctor holds onto the handle at the base of the needle probe, and pushes the sterilized needle probe through the skin (percutaneously) toward the bone in the direction that the needle points.

FIG. 4 shows the internal structure of the probe. The handle contains a load cell that senses force translated from the needle when piercing tissue to the right of the probe. When assembling the probe, the needle is inserted first into the front piece of the handle. The back piece of the handle is screwed to the front piece with the load cell in it and its loading area facing the needle base. Washers are placed in the assembly to eliminate free play between the load cell and the needle. The data cable from the load cell is exposed at the end of the probe and connected to the computer for data acquisition. Note that a piezoelectric force sensor can replace a load cell (which is a strain gauge) in this apparatus.

During a distal push for piercing tissue, the computer program acquires the force on the needle probe as it travels forward, while simultaneously recording the distance that the needle tip travels. The force that the needle base encounters, and the distance that the needle tip travels, are both one dimensional. The data acquisition is sampled at a high enough rate (e.g., 10 KHz) so that a typical force profile appears continuous and looks like the curves shown in FIG. 5. Shown in Panel A is the force (f) vs. distance (x) curve.

While the needle travels through a region of similar tissue (i.e, fat and muscle tissue), the resistant force at the base of the needle increases gradually. After the needle traverses across the soft tissue, it hits the bone tissue, causing a large increase of resistant force when the needle is pushed further forward. The arrows in FIG. 5 point to the needle piercing of the skin, and touching of the bone, respectively. Note that the force increases dramatically when the needle pierces the periosteum and cortical bone.

FIG. 5 Panel B shows the rate of change (i.e., the derivative) of force with respect to distance as a function of distance, i.e., $df/dx$ vs. x, after a smoothing filter is applied. Note that $df/dx$ peaks when the needle tip encounters tissue changes.

The bone surface can be detected when df/dx reaches a threshold, e.g., 1.0 N/mm or more. This threshold can be dynamically determined as it should increase when a deep layer of soft tissue has to be pierced before reaching the bone.

Biological samples from fresh animal bones with soft tissue attached were used to test the device. The results are shown in the attached TABLE 1. Because the true distance could not be accurately obtained, the error of measurement could not be calculated. Therefore, the offset to adjust to the real distance was not found there. However, standard deviation (std) was used to represent the spread of the distribution. The small standard deviation showed the high precision of the instrument.

When measuring the distance of the bone surface from the origin, the precision of the apparatus was high from the small standard deviations averaging at 0.11 mm (N=6).

The needle probe is preferably constructed of steel, with a diameter of 2 mm at the shaft. It has a symmetric tip. This construction, shown in FIG. 4, will ensure minimal bending of the needle; therefore, no steering is required when piercing through tissue. The location of the needle tip is accurately reflected by the calibrated Denavit and Hartenberg parameters of the tracking robot arm.

A needle-sized probe that can pierce the flesh surrounding the bone is a simple way of reaching the surface of the bone. However, it is important to accurately locate the surface of the bone and not unknowingly penetrate inside the bone with the sharp needle. Because it is difficult to control the force, and therefore the depth of the needle insertion action, the device should inform the surgeon where the needle probe is located in patient tissue.

Figure 1:
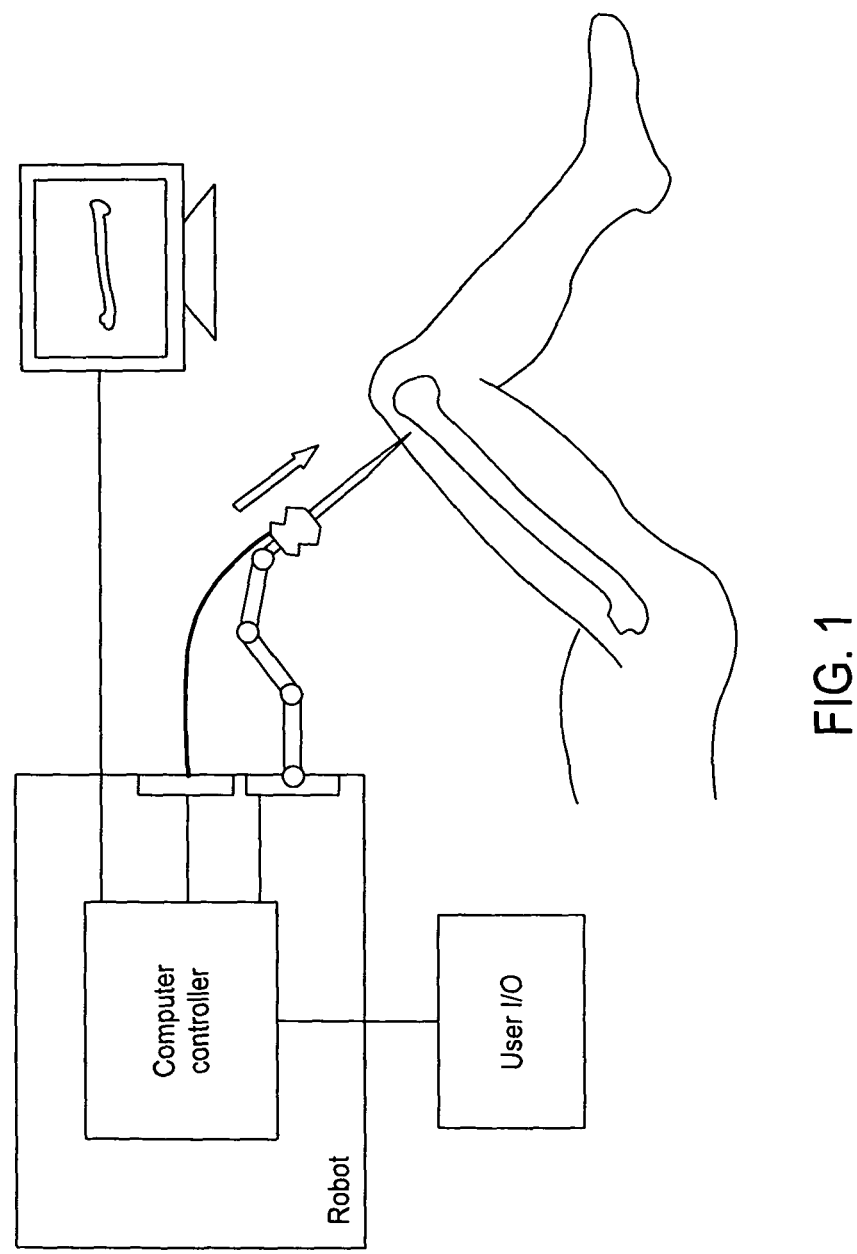
FIG. 1 shows a schematic diagram of the percutaneous bone detector with the patient lying down supine.

When the needle traverses through tissues from the skin to the bone, the resistant force acting on the needle will increase. The resistant force alone is not enough information to distinguish different tissues. However, by using the combination of resistant force and the distance traveled by the needle, it is possible to make the distinction. This is because the rate of increase of the force with respect to the distance changes as the needle tip reaches different kinds of tissue. To measure the force acting on the needle while knowing the location of the needle tip, an apparatus was built using a force sensor and tracking device with encoders. A computer is used to acquire and process the force and distance data. A schematic diagram of this apparatus is shown in FIG. 1.

With force sensor attached to the needle probe, the interface between two layers of tissue with different degrees of hardness can be distinguished via the rate of change of the force that the probe encounters. More particularly, when a piercing probe is pushed through tissue, it encounters varying resistance as it goes through different types of tissue. The current invention utilizes this varying resistance to distinguish between soft tissue (i.e., fat and muscle) and hard tissue (i.e., bone). The piecing probe in this invention is a large diameter steel needle. A load cell is attached to the probe base so that the resistant force is directly sensed by the load cell. The distance traveled by the needle tip is tracked by a set of encoders on an arm. Thus, the relationship between the force and distance can be measured.

Signal processing (such as to reduce noise) is performed so as to eliminate randomness due to "looseness" of the setup. The derivative of the force with respect to distance of the probe tip is calculated. A threshold is determined heuristically for the soft tissue-bone tissue interface. Different bone types, different sections of the bone, the age of the patient, and health of the patient all have an effect on the threshold.

Figure 2:
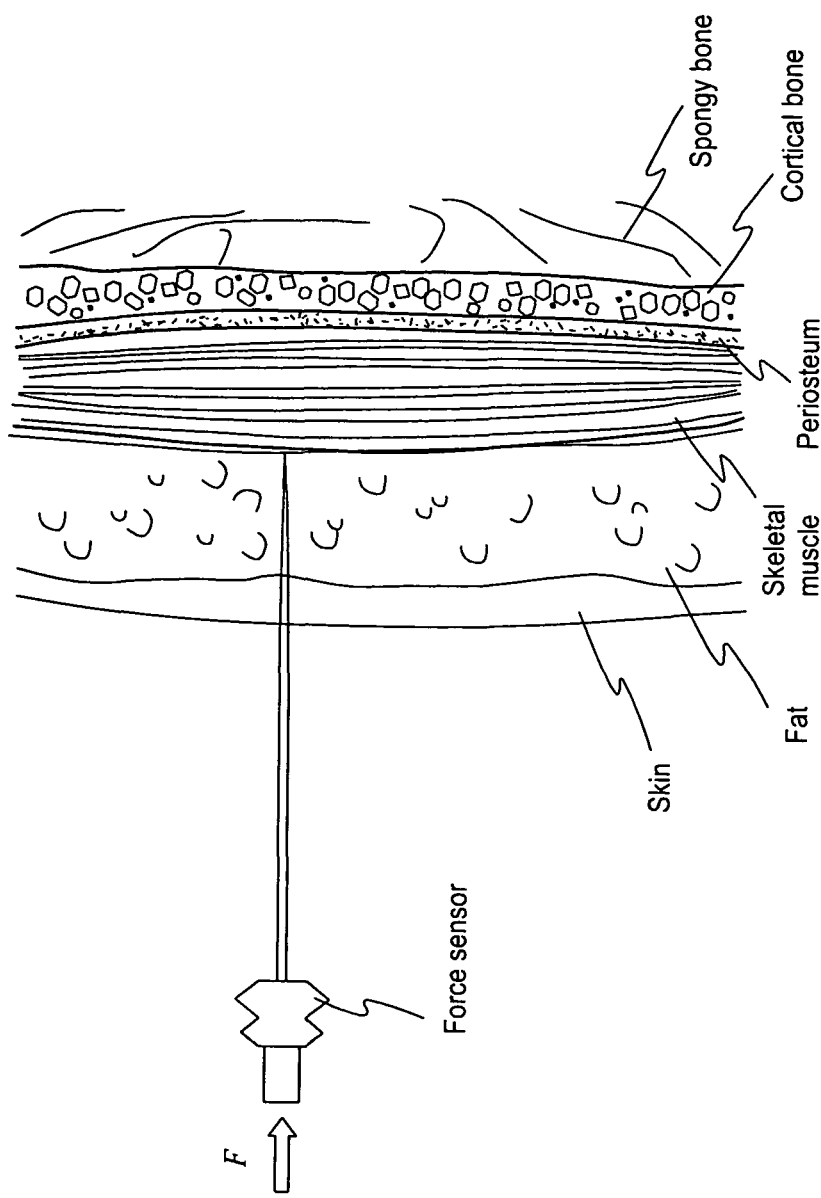
FIG. 2 shows an illustration of the percutaneous bone detector penetrating soft tissue centrally toward a bone.

FIG. 2 shows a detailed schematic diagram of the setup. The needle probe in the setup pieces through the skin and penetrates across different layers of tissues and reaches the bone of a limb. The setup measures the resistance acting on the needle and the travel (distance) of the needle. The computer digitizes the two measurements and processes them to obtain the bone surface information. In the plot, V stands for voltage; x stands for distance in mm.

FIGS. 6 and 7 illustrate object process diagrams (OPDs) that summarize the objects and process flows of various aspects of a preferred embodiment of the invention. In the OPDs, a square represents an object; an oval represents an action. An action is taken by an object or objects. The output is also an object. The overall OPD is shown in FIG. 6 while the detailed sub-processes of a major process of FIG. 6 is shown in FIG. 7.

In FIG. 6, the surgeon uses the probe on the patient to digitize a collection of bone surface points, preferably with direction and assistance from the computer. The output data from the data collection are processed by the computer to give bone surface information.

In FIG. 7, the action "Collect surface points" is described in detail. It is an iterative process. With each surface point datum collected, the computer processes and calculates the location of the surface point. It then compiles the information and determines if the another point datum needs be acquired by the doctor. This process continues until enough data points have been acquired in order to determine the current location of the bone in the robot system coordinate system. Once a sufficient number of data points have been collected, the doctor is instructed to stop and the data are passed to the surface process.

Thus, there has now been disclosed a novel resistant force-based needle probe system utilizing a mechano-electrical device that provides great precision and accuracy for determining bone position. As a result, this force-based device and method can be implemented on an off-the-shelf digitizer arm. This device and method makes minimally invasive procedures possible for locating bone surfaces.

FURTHER EXEMPLARY EMBODIMENTS OF THE PRESENT INVENTION

The probe is intended to make mechanical contact with the bony surface, and is thin enough, and long enough, so that it can be introduced through the soft tissue with minimal trauma until the tip of the probe contacts the bony surface.

In one preferred construction, the probe is a stainless steel needle, of 5 cm length and 0.6 mm diameter, and has a sharpen tip of symmetric shape.

In another form of the invention, the probe is a stainless steel probe, of 5 cm length and 1.2 mm diameter (in order to prevent bending of the probe), and has a dull tip to prevent the penetration of the bony surface.

For the means to record the spatial location of the probe, it needs to recognize the location of the probe tip so that when the probe is in contact with the bone, that location will be digitized and processed by the computer-aided surgery system. For recognizing the probe location, a mechanical arm-type digitizer, an infra-red (IR) marker tracking camera, a magnetic tracker or any other appropriate method and/or apparatus can be used.

In one preferred form of the invention, the mechanical arm-type digitizer is a mechanical arm which has at least 5 degrees of freedom and is equipped with encoders in order to detect the posture of the arm and thus calculate the location of the probe tip. By way of example but not limitation, the mechanical arm-type digitizer may comprise the MICRO- SCRIBE product sold by Immersion Co. or the Infinite 2.0 portable CMM product sold by Romer Inc.

In another form of the invention, an infra-red (IR) marker tracking camera is used, with the tracking system having a marker which emits infrared or reflect the infrared light, and having at least 2 cameras which have infrared filters so that the spatial location of the marker is calculated. By way of example but not limitation, the infra-red (IR) marker tracking camera may comprise the Polaris product sold by NDI Inc.

And in another form of the invention, a magnetic tracker is used, wherein a source generates a magnetic field and a sensor with electric coil detects the location of the sensor by the amount and direction of the magnetic field. By way of example but not limitation, the magnetic tracker may comprise the Patriot product sold by Polhemus Inc.

For the means to detect contact of the probe with the bony surface, various constructions may be used, e.g., a force sensor to detect the resistance of the material, a piezoelectric sensor to measure the natural frequency of the probe, an ultrasound sensor to measure the material property at the tip of the probe, or any other appropriate method or apparatus can be used.

By way of example but not limitation, where a force sensor is used to detect the resistance of the material, the force sensor may comprise a microswitch to the tip of the probe, so that the switch is activated by a certain amount of the force.

By way of further example but not limitation, a piezoelectric sensor may be used to measure the natural frequency of the probe. In this form of the invention, a piezoelectric actuator is attached to the probe, providing a vibration to the probe, and the natural frequency of the probe is measured as one end of the probe is contacting the hard (i.e., bone) material—contact with the hard bone will cause the natural frequency of the probe to be changed, so that contact with the bone will be detected.

By way of still further example but not limitation, where an ultrasound sensor is used to measure the material property at the tip of the probe, the probe may comprise a hollow shaft and one end is equipped with a piezoelectric ultrasound emitter and a receiver, and the elasticity at the tip of the probe is detected by the ultrasound receiver.

Some Significant Aspects of the Invention

Thus, in various forms of the invention, there is provided, among other things:

(1) A device for detecting the location of a bony surface, wherein the device consists of:
  a shallow diameter probe;
  a means to measure the location of the probe; and
  a means to detect contact of the probe with the bony surface.

(2) A device for detecting a bony surface, wherein the device consists of:
  a needle;
  a handle;
  a force sensor, located between the handle and the needle, to measure the insertion force of the needle;
  a tracker which measures the location of the handle to measure the insertion depth of the needle; and
  a signal processor to detect the contact of the needle with the bony surface, by monitoring the change of the insertion force.

(3) A device as above, wherein the needle is a thin metal element with a symmetric sharp tip.

(4) A device as above, wherein the signal processor continuously calculates the rate of the change of the insertion force.

(5) A method for categorizing the different interfaces from the skin to the cortical bone by the different rates of change of the resistive forces.

(6) A method for reconstructing the bone surface model by automatically collecting the points probed by inserting the needle at various locations with detected bone locations via the device as above.

(7) A method for automatically optimizing the specification of a set of probing locations so as to define a suitable spread of points within the needed area.

(8) A needle probe as above which has a flattened base to interface with a force sensor.

Modifications

It will be understood that many changes in the details, materials, steps and arrangements of parts, which have been herein described and illustrated in order to explain the nature of the invention, may be made by those skilled in the art without departing from the principles and scope of the present invention.

TABLE 1

Results from experiments with animal samples

| distance (mm) | needle diameter = 1.83 mm | | | needle diameter = 2.03 mm* | | |
|---|---|---|---|---|---|---|
| | bovine small | bovine small | bovine small | bovine large | swine foot meatless | swine foot |
| mean | 35.15 | 35.64 | 40.57 | 23.78 | 43.09 | 48.29 |
| std | 0.13 | 0.14 | 0.12 | 0.09 | 0.06 | 0.12 |

What is claimed is:

1. Apparatus for determining the position, in three dimensional space, of a bone covered by soft tissue, said apparatus comprising:
  a needle having a tip for penetrating soft tissue;
  position-determining means for determining the position of said tip of said needle in three-dimensional space;
  force-sensing means for sensing the level of force encountered by said tip of said needle;
  discriminating means for determining the rate of change in the level of force encountered by said tip of said needle in relation to the distance travelled by said needle so as to discriminate between (i) when said tip of said needle is engaging soft tissue, and (ii) when said tip of said needle is engaging bone;
  recording means for recording the position of said tip of said needle in three dimensional space when said discriminating means indicate that said tip of said needle is engaging bone; and
  processing means for receiving a plurality of data points from said recording means and, using the plurality of data points from said recording means, determining the position, in three dimensional space, of a bone covered by soft tissue.

2. A method for determining the position, in three dimensional space, of a bone covered by soft tissue, said method comprising:
  directing a tip of a needle through the soft tissue and toward the bone while sensing the level of force encountered by said tip of said needle;
  determining the rate of change in the level of force encountered by said tip of said needle in relation to the distance travelled by said needle;

identifying a spike in the rate of change in the level of force encountered by said tip of said needle in relation to the distance travelled by said needle, wherein the spike is reflective of said tip of said needle encountering bone;

recording the position of said tip of said needle in three-dimensional space when said spike is identified; and repeating the foregoing steps a sufficient number of times and determining the position, in three dimensional space, of a bone covered by soft tissue.

3. Apparatus for determining the position, in three dimensional space, of a first type of tissue which is covered by a second type of tissue, wherein said first type of tissue has a greater resistance to penetration than said second type of tissue, said apparatus comprising:

a needle having a tip for penetrating tissue;

position-determining means for determining the position of said tip of said needle in three-dimensional space;

force-sensing means for sensing the level of force encountered by said tip of said needle when engaging tissue;

discriminating means for determining the rate of change in the level of force encountered by said tip of said needle in relation to the distance travelled by said needle so as to discriminate between (i) when said tip of said needle is engaging said first type of tissue, and (ii) when said tip of said needle is engaging said second type of tissue;

recording means for recording the position of said tip of said needle in three dimensional space when said discriminating means indicate that said tip of said needle is engaging said first type of tissue; and processing means for receiving a plurality of data points from said recording means and, using the plurality of data points from said recording means, determining the position, in three dimensional space, of a bone covered by soft tissue.

4. A method for determining the position, in three dimensional space, of a first type of tissue which is covered by a second type of tissue, wherein said first type of tissue has a greater resistance to penetration than said second type of tissue, said method comprising:

directing a tip of a needle through the second type of tissue and toward the first type of tissue while sensing the level of force encountered by said tip of said needle;

determining the rate of change in the level of force encountered by said tip of said needle in relation to the distance travelled by said needle;

identifying a change in the rate of change in the level of force encountered by said tip of said needle in relation to the distance travelled by said needle, wherein said change is reflective of said tip of said needle encountering said first type of tissue;

recording the position of said tip of said needle in three-dimensional space when said change is identified; and repeating the foregoing steps a sufficient number of times and determining the position, in three dimensional space, of a bone covered by soft tissue.

\* \* \* \* \*